US012723237B2

(12) United States Patent
Baldeschi et al.

(10) Patent No.: US 12,723,237 B2
(45) Date of Patent: Sep. 1, 2026

(54) METHOD FOR OBTAINING ENDOTHELIAL CELLS FROM PLURIPOTENT STEM CELLS

(71) Applicants: ADHARA, Paris (FR); CENTRE D'ETUDE DES CELLULES SOUCHES, Corbeil Essonnes (FR); UNIVERSITE D'EVRY VAL D'ESSONNE, Evry (FR)

(72) Inventors: Christine Baldeschi, Villemoisson sur Orge (FR); Annabelle Darle, Favieres (FR)

(73) Assignees: ADHARA, Paris (FR); CENTRE D'ETUDE DES CELLULES SOUCHES, Corbeil Essonnes (FR); UNIVERSITE D'EVRY VAL D'ESSONNE, Evry (FR)

( * ) Notice: Subject to any disclaimer, the term of this patent is extended or adjusted under 35 U.S.C. 154(b) by 894 days.

(21) Appl. No.: 17/905,524

(22) PCT Filed: Mar. 2, 2021

(86) PCT No.: PCT/FR2021/050354
§ 371 (c)(1),
(2) Date: Sep. 2, 2022

(87) PCT Pub. No.: WO2021/176178
PCT Pub. Date: Sep. 10, 2021

(65) Prior Publication Data

US 2023/0183651 A1 Jun. 15, 2023

(30) Foreign Application Priority Data

Mar. 2, 2020 (EP) .................................... 20305215

(51) Int. Cl.
*C12N 5/071* (2010.01)

(52) U.S. Cl.
CPC ........... *C12N 5/069* (2013.01); *C12N 5/0698* (2013.01); *C12N 2501/01* (2013.01); *C12N 2501/115* (2013.01); *C12N 2501/155* (2013.01); *C12N 2501/165* (2013.01); *C12N 2501/727* (2013.01); *C12N 2506/02* (2013.01)

(58) Field of Classification Search
None
See application file for complete search history.

(56) References Cited

U.S. PATENT DOCUMENTS

2016/0186135 A1 6/2016 Thomson et al.
2020/0362315 A1* 11/2020 Taniguchi .............. A61K 35/51

FOREIGN PATENT DOCUMENTS

CN 109797132 A 5/2019
WO WO-2012168167 A1 * 12/2012 ......... G01N 33/5088

OTHER PUBLICATIONS

Flores-Nascimento, et al. CD144, CD146, and VEGFR-2 properly identify circulating endothelial cell. Revista Brasileira de Hematologia e Hemoterapia. 2015; 37(2):98-102. (Year: 2015).*

Miyazaki, et al. A novel strategy to engineer pre-vascularized 3-dimensional skin substitutes to achieve efficient, functional engraftment. 2019; 9:1-10. (Year: 2019).*

Lim, et al. Maintenance of hPSCs under xeno-free and chemically defined culture conditions. International Journal of Stem Cells. 2019; 12:484-496. (Year: 2019).*

StemFit Product Information Brochure. (Includes cover sheet with search parameters.) Accessed 2014. (Year: 2014).*

Lin, et al. A scalable and efficient bioprocess for manufacturing human pluripotent stem cell-derived endothelial cells. Stem Cell Reports. 2018; 11(2):454-469. (Year: 2018).*

Miyazaki, et al. A novel strategy to engineer pre-vascularized 3-dimensional skin substitutes to achieve efficient, functional engraftment. Scientific Reports. 2019; 9(1):1-10. (Year: 2019).*

Lim, et al. Maintenance of hPSCs under xeno-free and chemically defined culture conditions. International Journal of Stem Cells. 2019; 12(3):484-496. (Year: 2019).*

Haghighi, et al. bFGF-mediated pluripotency maintenance in human induced pluripotent stem cells is associated with NRAS-MAPK signaling. Cell Communication and Signaling. 2018; 16(1):1-14. (Year: 2018).*

Laco, et al. Unraveling the inconsistencies of cardiac differentiation efficiency induced by the GSK3β inhibitor CHIR99021 in human pluripotent stem cells. Stem Cell Reports. 2018; 10(6):1851-1866. (Year: 2018).*

Makoto Sahara et al, "Manipulation of a VEGF-Notch signaling circuit drives formation of functional vascular endothelial progenitors from human pluripotent stem cells", Cell Research, vol. 24, No. 7, May 9, 2014 (May 9, 2014), p. 820-841.

Liu Xiaopeng et al, "Differentiation of functional endothelial cells from human induced pluripotent stem cells: A novel, highly efficient and cost effective method", Differentiation, Springer Verlag, DE, vol. 92, No. 4, Jun. 4, 2016 (Jun. 4, 2016), p. 225-236.

Hannah K. Wilson et al, "Concise Review: Tissue-Specific Microvascular Endothelial Cells Derived From Human Pluripotent Stem Cells : Stem Cell-Derived Tissue-Specific Endothelial Cells", Stem Cells (Miamisburg), vol. 32, No. 12, Nov. 26, 2014 (Nov. 26, 2014), p. 3037-3045.

Gopu Sriram et al, "Efficient differentiation of human embryonic stem cells to arterial and venous endothelial cells under feeder- and serum-free conditions", Stem Cell Research & Therapy, vol. 6, No. 1, Dec. 1, 2015 (Dec. 1, 2015).

Xiaojun Lian et al, "Efficient Differentiation of Human Pluripotent Stem Cells to Endothelial Progenitors via Small-Molecule Activation of WNT Signaling", Stem Cell Reports, vol. 3, No. 5, Nov. 1, 2014 (Nov. 1, 2014), p. 804-816.

Patsch, C. et al., "Generation of vascular endothelial and smooth muscle cells frum human pluripotent stem cells", Nat Cell Biol. 17 No. 8, Aug. 2015.

* cited by examiner

*Primary Examiner* — Allison M Fox
*Assistant Examiner* — Gina Pronzati
(74) *Attorney, Agent, or Firm* — WCF IP

(57) ABSTRACT

The invention relates to a method for obtaining endothelial cells from human pluripotent stem cells.

15 Claims, 6 Drawing Sheets

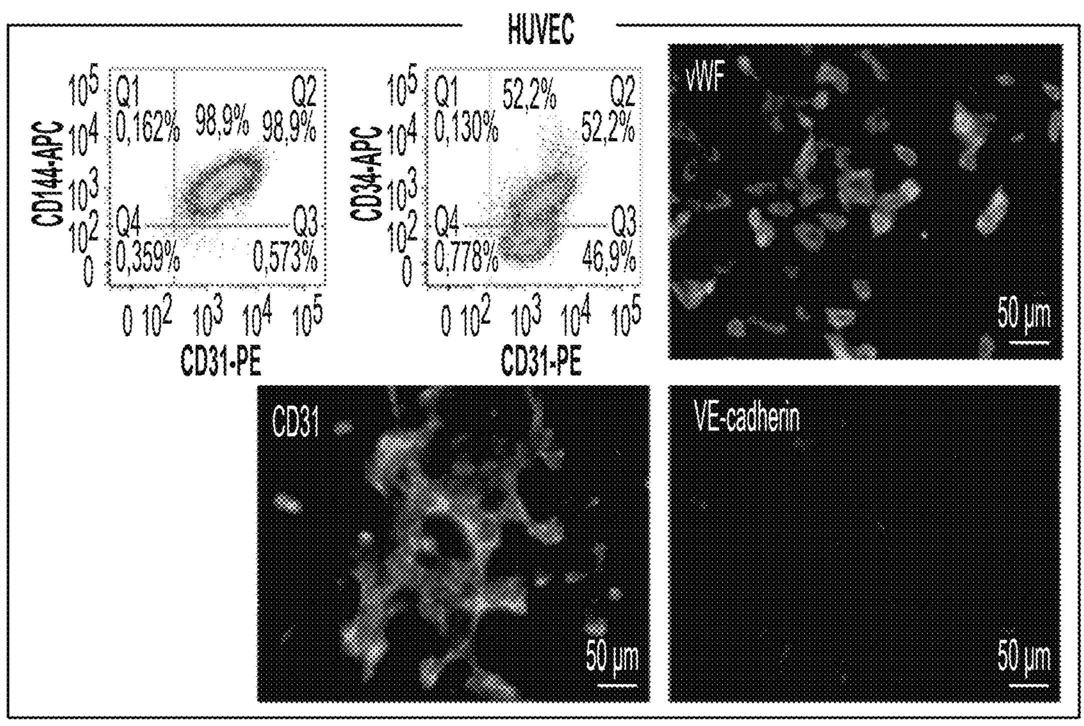
FIG. 1C.a
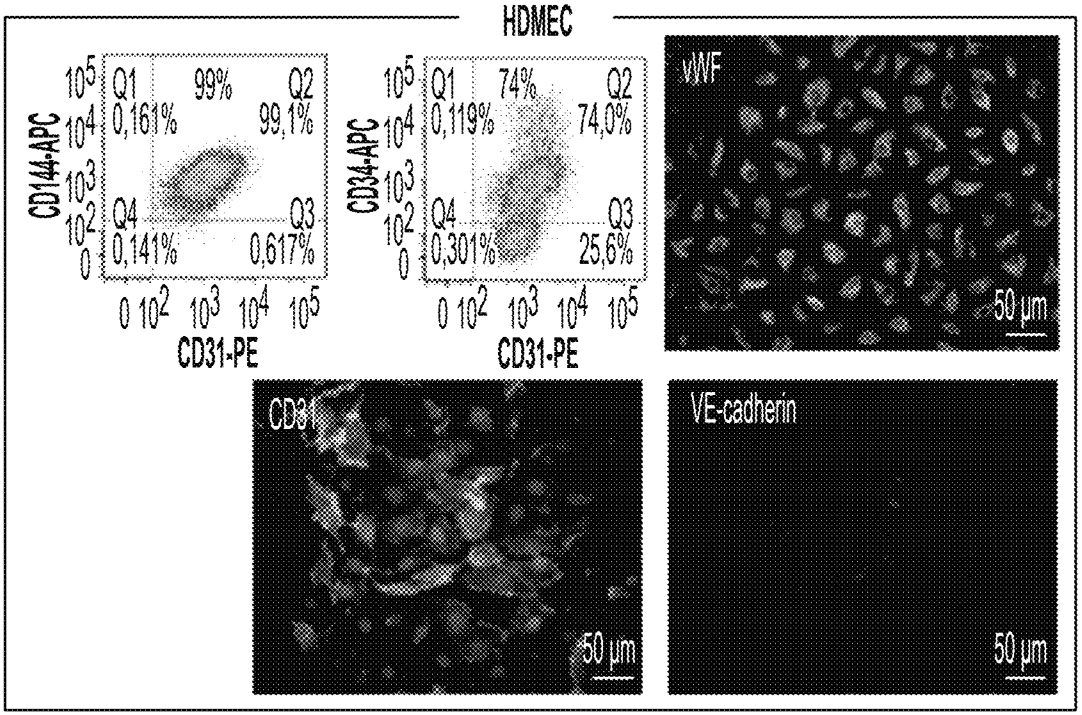
FIG. 1C.b

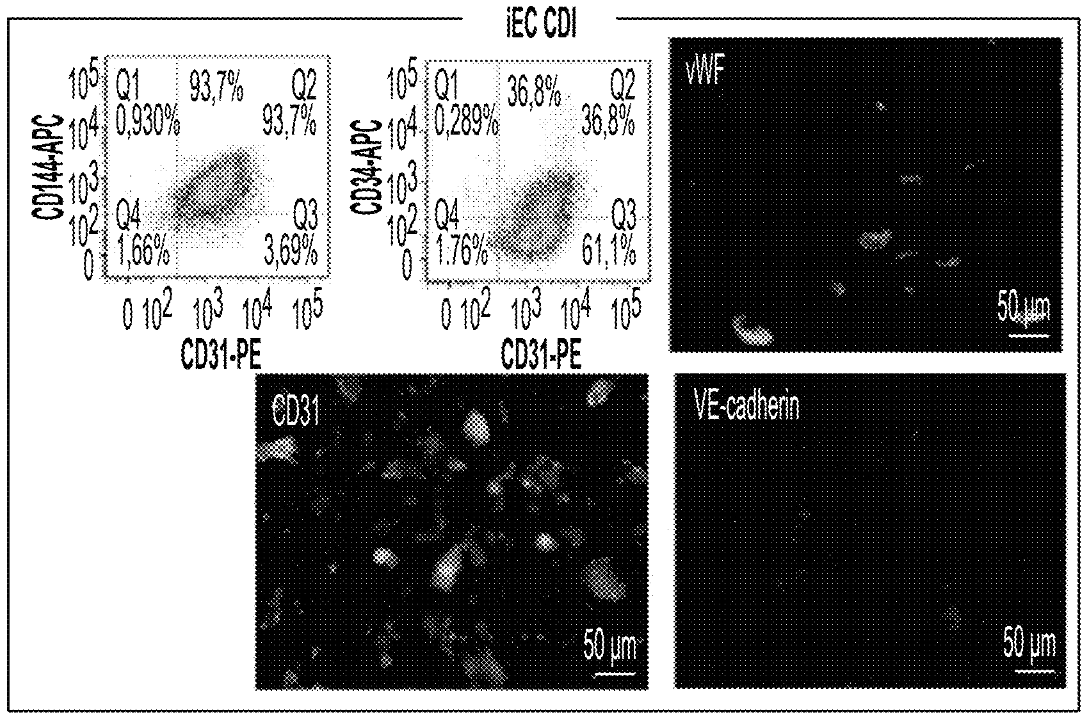
FIG. 1C.c

METHOD FOR OBTAINING ENDOTHELIAL CELLS FROM PLURIPOTENT STEM CELLS

The present invention relates to a method for obtaining endothelial cells from embryonic pluripotent stem cells (or PSCs) or from induced pluripotent stem cells (iPSs).

Context of the Invention

Human pluripotent stem cells, whether they are embryonic or induced to pluripotency, have a capacity to proliferate identically (each parent cell giving rise to two daughter cells identical to the first) ad infinitum, without ever entering into senescence as all the other cells of the body do, and the capacity, under other culture conditions, to differentiate to give rise to any cell of the body (ectoderm, endoderm and mesoderm).

Stem cells are important in regenerative medicine (source of major and promising interest for succeeding in producing organs), for modeling, notably diseases, and pharmacological screening.

Pluripotent stem cells appear to be a possible alternative because of their unlimited proliferation property and their differentiation capacity making it possible to obtain, from a single donor, all the cell types of interest in large amount. Furthermore, pluripotent stem cells make it possible to obtain a homogeneous population of differentiated cells, unlike primary cultures (heterogeneity, limited numbers, risk of senescence).

The present invention targets a method for obtaining endothelial cells, under conditions referred to as "clinical", that is to say conditions where the products used are manufactured according to good manufacturing practices (GMP) and can therefore be used in clinical studies, unlike "research"-grade products which can only be used for research.

"GMP" standards constitute a notion of quality assurance established by the European (or American) commission in the context of the manufacture of medicaments for human or veterinary use (Eudralex in France or FDA in the United States). They were created to limit the risks of product cross-contamination, by emphasizing hygiene practices, and also the risks of confusion: labeling/identification.

The principles of GMP make obligatory the writing of protocols and instructions allowing productions of uniform quality with compliant traceability. They also integrate processes, product quality and safety of personnel. GMP are currently organized into 3 parts:

- Good manufacturing practices for medicaments for human use.
- Good manufacturing practices for active substances used as starting material in medicaments.
- Documents relating to good manufacturing practices giving the recommendations on the international requirements for batch certification.

To establish protocols for obtaining "clinical" endothelial cells, the starting materials must meet the same GMP standards. The products used are therefore entirely defined in terms of their compositions, their concentrations, their origins and their levels of sterility.

To date, there is no means for obtaining endothelial cells in large amount according to GMP standards. However, the needs for such cells are increasingly numerous, in various fields of clinical application, such as the obtaining of reconstituted tissues that can be used in therapy.

HUVEC cells (Human Umbilical Vein Endothelial cells) are endothelial cells from human umbilical cord blood. They can be obtained in large amount. However, they can exhibit problems of heterogeneity and there is a risk of the batches exhibiting variability depending on donors.

Pluripotent stem cells appear to be a possible alternative because of their unlimited proliferation property and their differentiation capacity making it possible to obtain, from a single donor, all the cell types of interest in large amount.

To date, there is no method for differentiating into endothelial cells starting from pluripotent human stem cells which meets GMP standards.

SUMMARY OF THE INVENTION

The present invention relates to a method for obtaining endothelial cells from human pluripotent stem cells of embryonic origin or induced human pluripotent stem cells, which meets GMP standards.

More particularly, the present invention relates to a method for differentiating into endothelial cells from human pluripotent stem cells, characterized in that:

a) on D0, the human pluripotent stem cells are dissociated, seeded at a density of from 40 000 to 60 000 cells/cm$^2$, preferably approximately 50 000 cells/cm$^2$, on a matrix and cultured in the presence of a medium suitable for the culture of pluripotent cells, further comprising fibroblast growth factor 2 (FGF2) and a ROCK inhibitor, b) on D1, the medium is replaced with a medium suitable for mesoderm induction, further comprising a GSK3 (Glycogen Synthase Kinase 3) inhibitor and BMP4 (Bone Morphogenetic Protein 4);

c) on D4, the medium is replaced with a medium suitable for the culture of endothelial cells, further comprising VEGF (Vascular Endothelial Growth Factor) and forskolin;

d) on D6, the cells are dissociated and selected for expression of the CD144 marker.

Advantageously, all the culture media and agents used are chemically defined and contain no additive of animal origin not controlled to the standards of Good Manufacturing Practices (or GMP).

The term "pluripotent stem cells" is intended to mean any undifferentiated cell capable of self-renewing ad infinitum, and differentiating into any cell type (ectoderm, endoderm, mesoderm). Preferably, the pluripotent stem cells according to the invention are human pluripotent stem cells (hPSCs).

In one embodiment, the pluripotent stem cells are human embryonic stem cells (hESCs).

There are many hESC lines, including the RC-9 (Roslin Cells 9) line, which was developed as a clinical-grade hESC line.

In one preferred embodiment, the human pluripotent stem cells are obtained by methods which do not require the destruction of embryos.

In another embodiment, the stem cells are human stem cells induced to pluripotency (human induced pluripotent stem cells or hiPSCs). There are numerous hiPSC lines that are commercial or have been produced according to the various existing reprogramming techniques (episome, mRNA, Sendai viral vector).

According to one embodiment of the invention, the pluripotent stem cells are specific hiPSC cells from a donor, obtained by reprogramming of peripheral blood mononuclear cells from said donor. The protocols for reprogramming peripheral blood mononuclear cells from the donor or CD34+ cells isolated from umbilical cord blood are known to those skilled in the art.

The term "matrix" or "coating" is intended to mean any substrate allowing the monolayer culture of stem cells. Preferably, the matrix used in the method according to the invention is a defined protein matrix. Preferably, the matrix is chosen from the group consisting of Matrigel™ L7 Coating™, laminin and vitronectin. Particularly preferably, the matrix is the L7™ matrix sold by Lonza under the reference FP-5020.

The expression "medium suitable for the culture of pluripotent cells" is intended to mean any medium which contains the nutrients and factors allowing the in vitro culture of pluripotent cells.

Preferably, the medium suitable for the culture of pluripotent cells is chosen from the iPS Brew XF GMP medium sold by Miltenyi Biotec and the iPS Stempro medium sold by ThermoFisher.

During step a), the medium is supplemented with fibroblast growth factor 2 or FGF2. Typically, the FGF2 is used at a final concentration of from 5 to 20 ng/ml, preferably approximately 10 ng/ml.

During step a), the medium is supplemented with a ROCK inhibitor. Preferably, the ROCK inhibitor is provided within the Revitacell supplement sold by Gibco.

The expression "medium suitable for mesoderm induction" is intended to mean any medium which contains the nutrients and factors allowing induction of the mesodermal pathway of pluripotent cells. Preferably, the medium suitable for mesoderm induction comprises the N2 and B27 supplements. The N2B27 medium is a 1:1 mixture of CTS KO DMEM-F12 medium and CTS Neurobasal medium, supplemented with CTS Glutamax, CTS N2 and CTS B27.

During step b), the medium suitable for mesoderm induction further comprises a GSK3 inhibitor and BMP4.

Optionally, after step c), on D5 the medium is again replaced with a medium suitable for the culture of endothelial cells, further comprising VEGF (Vascular Endothelial Growth Factor) and forskolin.

Those skilled in the art have, at their disposal, a certain number of agents known to inhibit the GSK3 kinase. Typically, the GSK3 inhibitor may be Chir99021 sold by Tocris.

Typically, the final concentration of Chir99021 is between 5 and 10 μM, preferably approximately 6 μM.

Typically, the final concentration of BMP4 is between 15 and 50 ng/ml, preferably approximately 25 ng/ml.

The expression "medium suitable for the culture of endothelial cells" is intended to mean any medium which contains the nutrients and factors allowing the in vitro culture of endothelial cells.

Preferably, the medium suitable for the culture of endothelial cells is the CnT-Endo medium sold by CellnTec.

During step c), the medium is supplemented with VEGF and forskolin.

Preferably, the VEGF is provided at a final concentration of between 100 and 300 ng/ml, even more preferably approximately 200 ng/ml.

Preferably, the forskolin is provided at a final concentration of between 1 and 3 μM, even more preferably approximately 2 μM.

According to one embodiment of the invention, the medium is renewed on D5.

On D6, a certain portion of the cell population has differentiated into endothelial cells.

In order to enrich the population with endothelial cells, a selection step is carried out in step d). This selection can be carried out by cell sorting.

According to one embodiment, the selection is carried out by flow cytometry.

According to another embodiment, the selection is carried out using magnetic beads covered with an antibody specific for the endothelial cell marker, such as CD34+ or CD144 or CD31+, preferably CD144.

The present invention also relates to an endothelial cell population directly obtained by the method described above. Advantageously, the endothelial cell population is homogeneous, that is to say that more than 90%, preferably more than 95%, more than 98%, or more than 99% of the cells are positive for the CD144 marker.

The present invention also relates to the use of the endothelial cell population for the production of a tissue, preferably a dermal tissue or skin substitute.

BRIEF DESCRIPTION OF THE FIGURES

Other characteristics, details and advantages of the invention will emerge on reading the appended figures.

(A) Morphology of the HUVEC, HDMEC and CDI iEC reference endothelial cells. (B) Transcriptomic profile of the reference cells, qPCR analysis of the endothelial cell-specific markers PECAM1 (or CD31), CD34, KDR, VE-cadherin (or CD144) and vWF. (C) Protein profile, analysis by FACS of CD31/CD34 and CD31/CD144 and by immunofluorescence of CD31, VE-cadherin (or CD144) and vWF. a) HUVEC, b) HDMEC, c) CDI iEC. (D) Functionality: formation of tubules on GFR-Matrigel, Ac-LDL endocytosis, response to inflammation by treatment with TNFα and observation of ICAM expression.

FIG. 2 represents the method according to the invention and the characterization of the endothelial cells obtained.

(A) Validated clinical protocol. (B) CD144-APC FACS on D6 (before selection). (C) FACS during the passages for the analysis of the CD31/CD144 and CD31/CD34 co-labelings with the results at P2 representative of the various passages. (D) Functionality of the cells produced during the passages and formation of tubules on GFR-Matrigel.

EXAMPLE 1: CHARACTERIZATION OF THE REFERENCE ENDOTHELIAL CELLS

HUVEC (Human Umbilical Vein Endothelial Cells) and HDMEC (Human Dermal Microvascular Endothelial Cells) primary endothelial cells and also iPS-derived endothelial cells produced by Cellular Dynamics International (CDI iEC) were used as reference cells for carrying out all the setting up and validation of the quality controls for the iPS-derived endothelial cells: transcriptomic profile (q PCR), protein profile (FACS, immunofluorescence) and functionalities (formation of tubules on Matrigel, response to inflammation, endocytosis capacity).

The markers analyzed in order to characterize the endothelial cells are CD31 encoded by the PECAM1 gene and CD144 encoded by the VE-cadherin gene, two membrane proteins involved in the intercellular junctions between endothelial cells and which enable endothelium integrity. The vWF cytoplasmic marker is involved in the platelet recruitment during a vessel lesion and is present in mature endothelial cells. It thus makes it possible to have an idea of the maturity of the cells. The CD34 protein is a marker common to endothelial and hematopoietic cells since it is expressed from the hemangioblast stage, said hemangioblast being the precursor of the two cell types. The final marker analyzed is VEGFR2 encoded by KDR, which is the VEGF receptor that itself is involved in angiogenesis stimulation and endothelial cell survival.

Figure 1A:
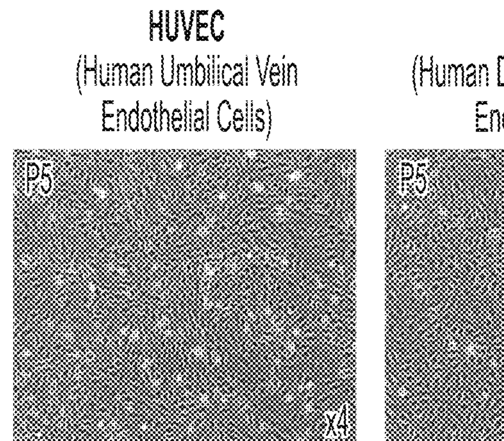
FIG. 1 represents the characterization of the reference endothelial cells on P5.
Figure 1A:
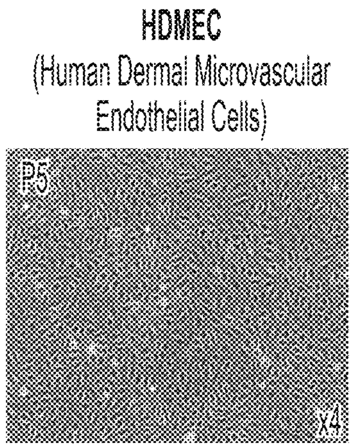
Figure 1A:
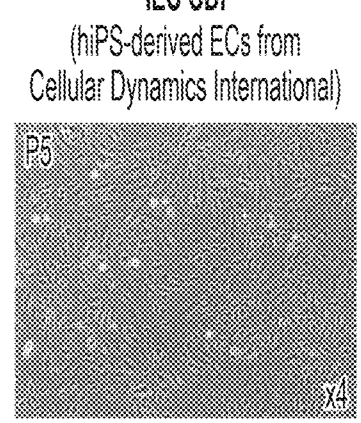
Figure 1B:
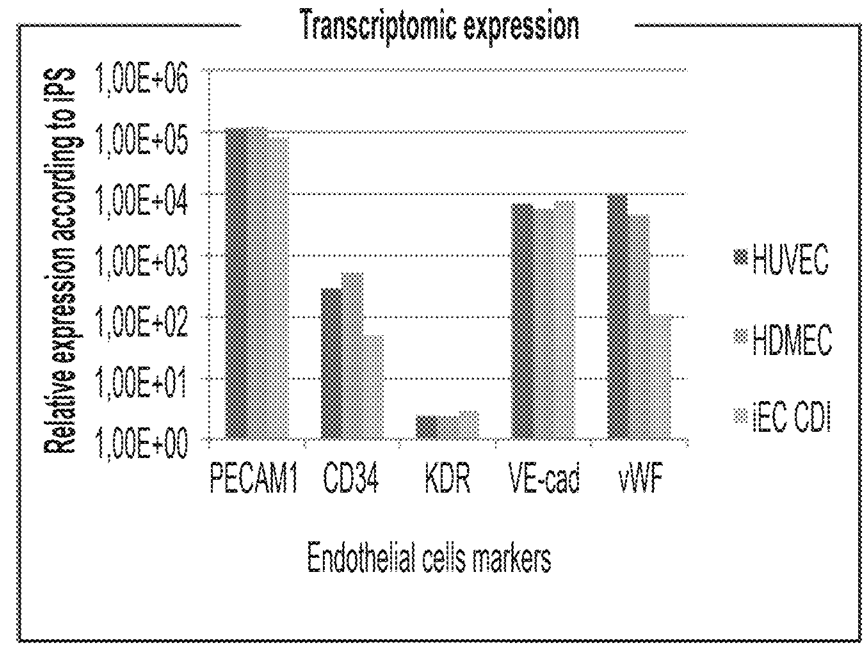

FIG. 1A shows that the 3 reference cell types exhibit the same morphology. They have a similar transcriptomic profile except for the vWF marker which shows a weaker maturity of the CDI iECs compared to the HUVEC and HDMEC (FIG. 1). The HUVEC and HDMEC show more than 98% expression of the CD31 and CD144 membrane markers. The CDI iECs show 93.7% expression of said markers. As for the CD34 marker, a double population, one which is positive and one which is negative to the extent of approximately 50%, is observed for the 3 cell types. The immunofluorescence makes it possible to verify that the vWF maturity marker is indeed expressed in the cytoplasm of the cells (FIG. 10 a, b and c).

Figure 1D:
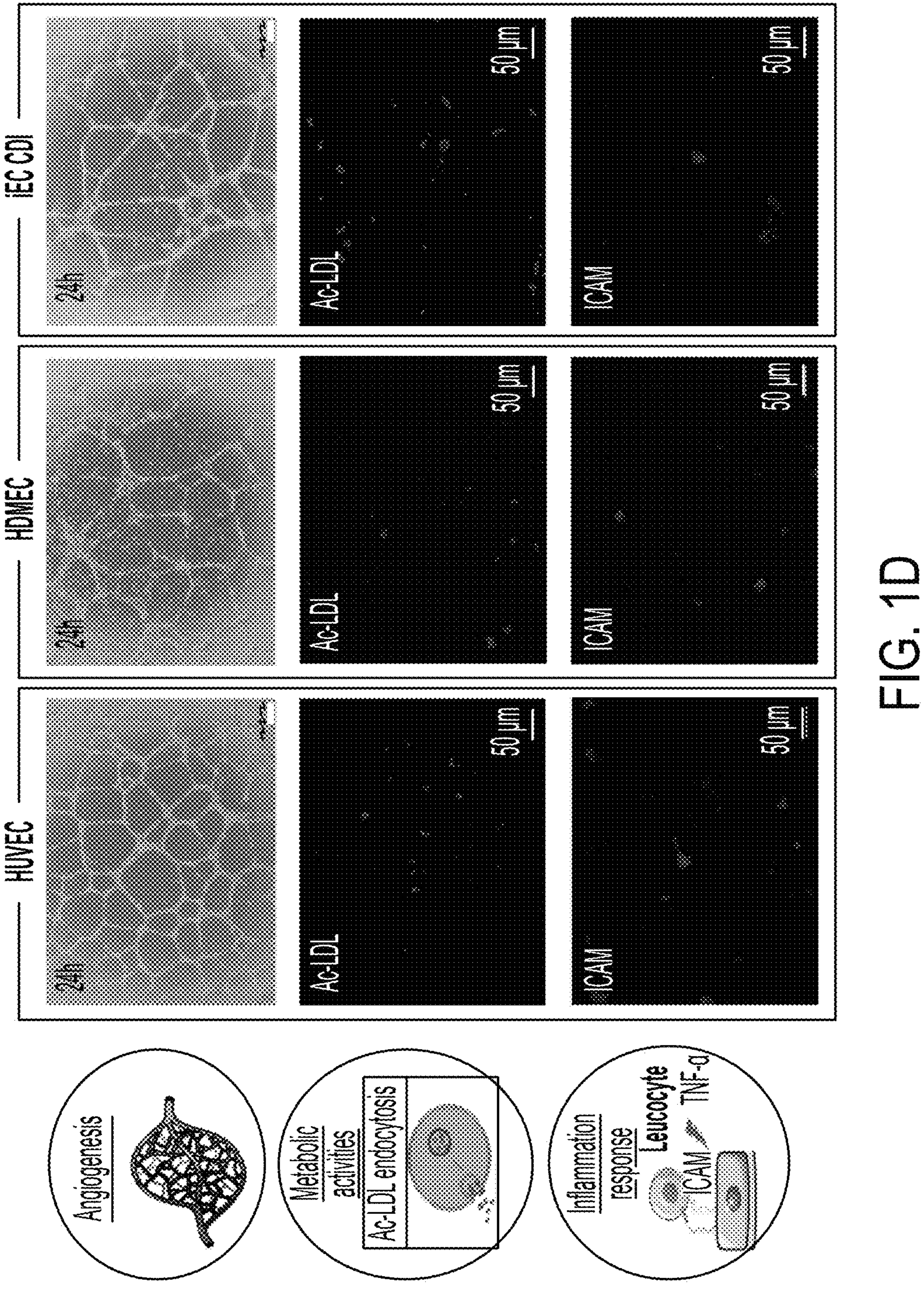

To verify the functionality of the cells, their ability to become organized in a "tubule-like" structure is tested on Matrigel for 24 h. The 3 control cell lines form structures in a network (FIG. 1D).

The metabolic activity of the endothelial cells is tested by means of the test for endocytosis of Ac-LDL coupled to a fluorochrome. The latter is added to the culture medium of the cells for 4 h and then the cells are rinsed. The endocytosed Ac-LDL remains in the cells and can be observed by the presence of fluorescence inside the cells, demonstrating their endocytosis capacity (FIG. 1D).

The aim of the final test for functionality of the endothelial cells is to show their ability to respond to inflammation via stimulation with TNFα for 24 h. This treatment enables the overexpression of ICAM, an inflammation marker (stimulator of adhesion and transmigration of leukocytes through the endothelial epithelium). Without treatment, no ICAM expression is observed in the cells (not shown), whereas, with treatment, the cells express ICAM in a similar manner between the 3 cell types (FIG. 1D).

These results show that the reference cells appear to be functional and express the endothelial cell-specific markers. These are therefore good controls for the cells derived from differentiations from pluripotent stem cells.

EXAMPLE 2: OBTAINING OF HPSC-DERIVED ENDOTHELIAL CELLS AND PHENOTYPIC CHARACTERIZATION OF SAID CELLS

The hiPSC cells are dissociated with accutase and then seeded at 50 000 c/cm$^2$ on L7 coating in Stempro hESC SFM medium supplemented with 10 ng/ml of FGF2 and Revitacell at 1/100. The following day, on D1, the medium is replaced with mesoderm induction medium: CTS N2B27 medium (1:1 mixture of KO DMEM-F12 and CTS neurobasal medium supplemented with CTS glutamax, CTS N2 and B27) with Chir99021 at 6 μM and BMP4 at 25 ng/ml.

On D4, the medium is replaced with the endothelial specification medium: CnT-ENDO medium supplemented with 200 ng/ml of VEGF and 2 μM of forskolin. The medium is renewed the following day. On the 6th day of differentiation, the differentiated cells are dissociated with accutase and selected using CD144+ magnetic beads with LS columns sold by Miltenyi Biotec. The positive cells, that is to say the differentiated endothelial cells, are collected and then frozen in CryoStor.

The cells are then thawed and seeded on a matrix of collagen I at 10 μg/ml at 20 000 c/cm$^2$ in CnT-ENDO medium supplemented with 50 ng/ml of VEGF. The medium is changed every 2 days and the cells are passaged every 3-4 days.

Figure 2A:
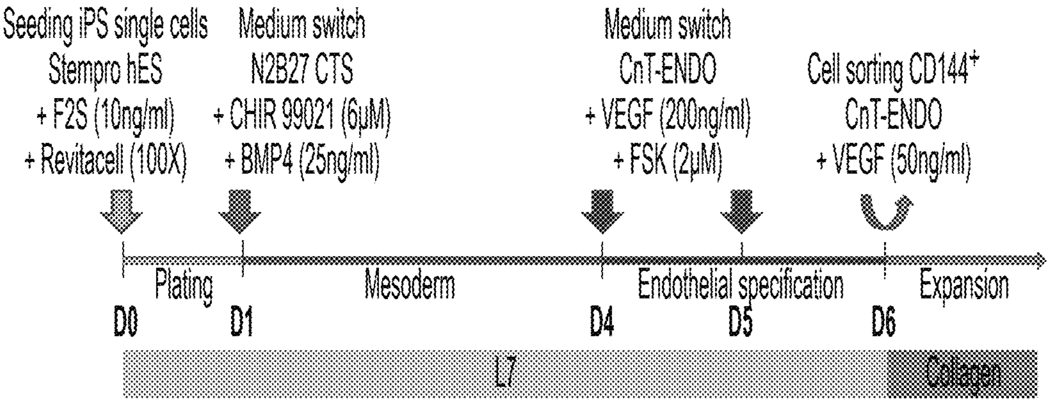
Figure 2B:
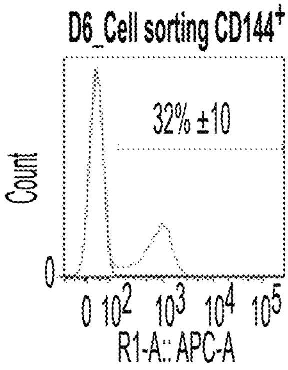
Figure 2C:
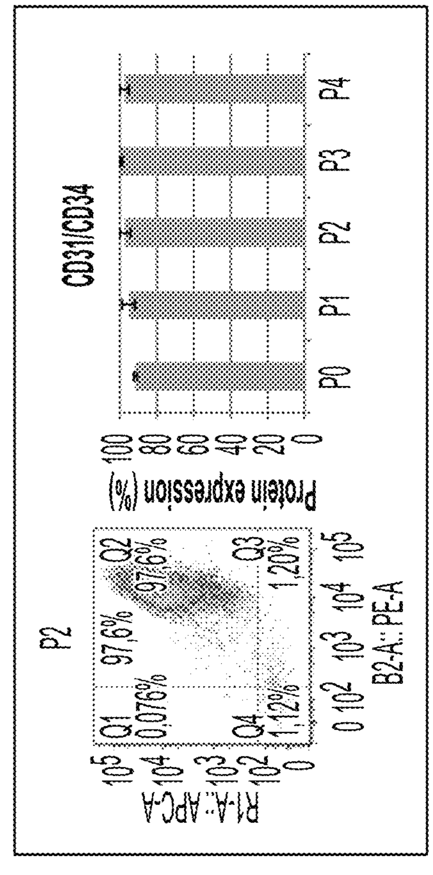

All of these steps are shown schematically in FIG. 2A.

Figure 2D:
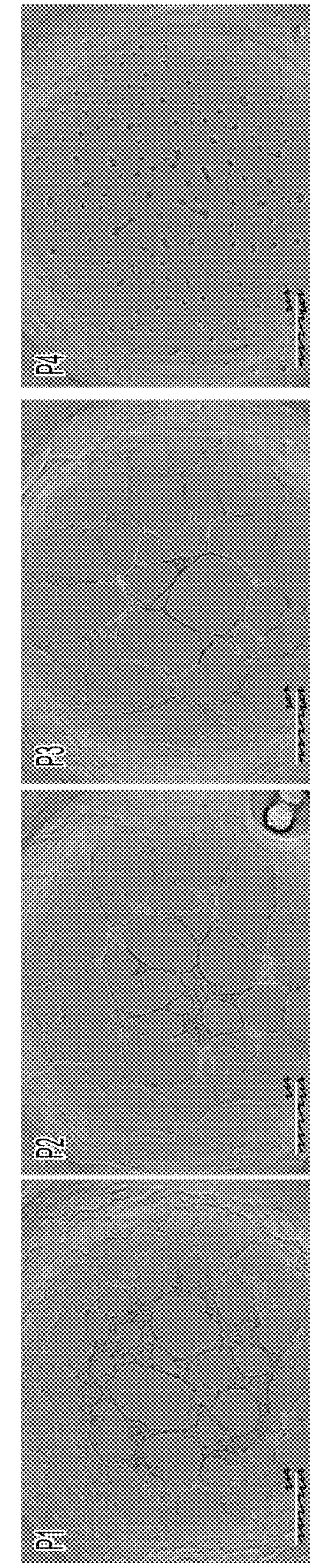
Figure 2D:
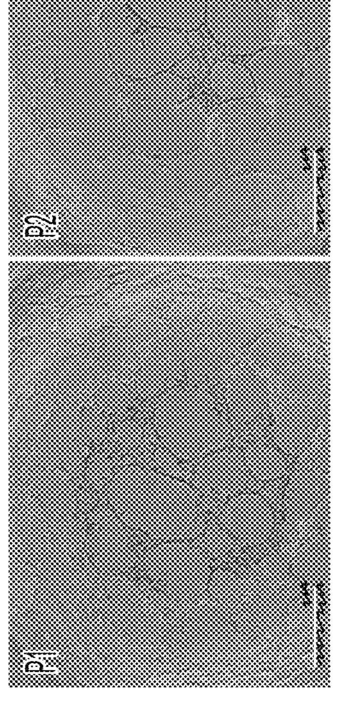

The cells thus obtained by this method were characterized from the phenotypic and functional point of view. The cells obtained by the method of the invention clearly express the CD31, CD144 and CD34 markers (FIG. 2C) and are functional up to P3 (FIG. 2D).

EXAMPLE 3: COMPARISON OF VARIOUS CULTURE MEDIA AND OF VARIOUS COATINGS

The protocol of example 2 was carried out using various culture media and various coatings, as indicated in table 1 below.

TABLE 1

| Experiment | iPS medium | Coating | Mesoderm induction | Endothelial specification | % CD144+ before selection |
|---|---|---|---|---|---|
| CR1 | iPS Brew XF | GFR-Matrigel | N2B27 | SP34SFM | 10.5 |
| | Stempro hES SFM | | | | 28.5 |
| | iPS Brew XF GMP | | | | 5.01 |
| C1 | Stempro hES SFM | L7 | N2B27 CTS | SP34SFM | 14.9 |
| | | | | HSC | 21.8 |
| | | | | Cnt-ENDO | 30.5 |
| | iPS Brew XF GMP | L7 | N2B27 CTS | SP34SFM | 21.2 |
| | | | | HSC | 19.7 |
| | | | | Cnt-ENDO | 32.9 |

The yields obtained (in % of CD144-positive (or CD144+) cells at the outcome of the differentiation step) were compared.

It results from these tests that the Stempro hES SFM and iPS Brew XF GMP media are both efficient as pluripotent cell culture medium.

The L7 coating, which is of clinical grade, is as efficient as the GFR-Matrigel coating.

For the mesoderm induction step, the CnT-ENDO medium is more efficient than the other media tested.

The invention claimed is:

1. A method for differentiating pluripotent stem cells into endothelial cells, comprising the steps of:

a) on day 0, the pluripotent stem cells are dissociated, seeded at a density of 40 000 to 60 000 cells/cm$^2$ on a matrix and cultured in monolayer conditions in the presence of a medium suitable for the culture of pluripotent cells, further comprising fibroblast growth factor 2 (FGF2) and a ROCK inhibitor;

b) on day 1, the medium is replaced with a medium suitable for mesoderm induction, further comprising a GSK3 (Glycogen Synthase Kinase 3) inhibitor and BMP4 (Bone Morphogenetic Protein 4);

c) on day 4, the medium is replaced with a medium suitable for the culture of endothelial cells, further comprising VEGF (Vascular Endothelial Growth Factor) and forskolin;

d) on day 6, the cells are dissociated and selected for expression of the CD144 marker, wherein said process meets good manufacturing practices (GMP) standards.

2. The method according to claim 1, wherein the FGF2 is used at a concentration from 5 to 20 ng/ml in step a).

3. The method according to claim 1, wherein the GSK3 inhibitor is Chir99021 in step b).

4. The method according to claim 1, wherein the BMP4 is used at a concentration between 15 and 50 ng/ml in step b).

5. The method according to claim 1, wherein the VEGF is used at a concentration between 100 and 300 ng/ml in step c).

6. The method according to claim 1, wherein the forskolin is used at a concentration between 1 and 3 μM in step c).

7. The method according to claim 1, wherein the pluripotent stem cells are human induced pluripotent stem cells.

8. The method according to claim 1, wherein the FGF2 is used at a concentration of approximately 10 ng/ml in step a).

9. The method according to claim 1 wherein the GSK3 inhibitor is Chir99021, at a concentration of 5 to 10 μM in step b).

10. The method according to claim 1 wherein the GSK3 inhibitor is Chir99021, at a concentration of 6 μM in step b).

11. The method according to claim 1, wherein the BMP4 is used at a concentration of 25 ng/ml in step b).

12. The method according to claim 1, wherein the VEGF is used at a concentration of 200 ng/ml in step c).

13. The method according to claim 1, wherein the forskolin is used at a concentration of 2 μM, in step c).

14. The method according to claim 1, wherein on day 0, the pluripotent stem cells are seeded at a density of 50 000 cells/$cm^2$.

15. A method for producing a dermal tissue, comprising obtaining endothelial cells by the method of claim 1, and producing the dermal tissue from the endothelial cells.

* * * * *